(12) United States Patent
Wang et al.

(10) Patent No.: US 9,974,587 B2
(45) Date of Patent: May 22, 2018

(54) PZT TRANSDUCER-HORN INTEGRATED ULTRASONIC DRIVING STRUCTURE

(71) Applicant: DALIAN UNIVERSITY OF TECHNOLOGY, Liaoning (CN)

(72) Inventors: Rui Wang, Liaoning (CN); Xuyue Wang, Liaoning (CN); Xiaoming Wang, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days. days.

(21) Appl. No.: 15/525,916

(22) PCT Filed: Sep. 13, 2015

(86) PCT No.: PCT/CN2015/089483
§ 371 (c)(1),
(2) Date: May 10, 2017

(87) PCT Pub. No.: WO2016/082602
PCT Pub. Date: Jun. 2, 2016

(65) Prior Publication Data
US 2017/0325864 A1 Nov. 16, 2017

(30) Foreign Application Priority Data
Nov. 27, 2014 (CN) .......................... 2014 1 0707662

(51) Int. Cl.
H01L 41/04 (2006.01)
A61B 17/86 (2006.01)
(Continued)

(52) U.S. Cl.
CPC .... *A61B 17/8665* (2013.01); *A61B 17/00234* (2013.01); *A61B 2017/00402* (2013.01); *A61B 2017/320088* (2013.01)

(58) Field of Classification Search
CPC ................................................. A61B 17/8665
(Continued)

(56) References Cited

U.S. PATENT DOCUMENTS 3,396,285 A * 8/1968 Minchenko ........... B06B 1/0618
310/325
4,352,570 A * 10/1982 Firth .................... B01D 15/206
241/175
(Continued)

*Primary Examiner* — J. San Martin
(74) *Attorney, Agent, or Firm* — Muncy, Geissler, Olds & Lowe, P.C.

(57) ABSTRACT

A PZT transducer-horn integrated ultrasonic driving structure consists of a nut, a bolt, a left PZT circular stack, a flange, a right PZT truncated stack and a horn. The horn, the right PZT truncated stack, the flange and the left PZT circular stack are arranged in sequence and connected via the bolt and then fastened via the nut; the right PZT transducer is a truncated cone-shaped stack formed by PZT circular plates; and the right PZT transducer and the horn are integrated to form the ultrasonic driving structure. Considering the dimension of PZT on two sides of the flange and the horn meet the requirements for ultrasonic vibration node and antinode, the dimension of round contour of the circular PZT stack and flange is reduced to increase the thickness of the truncated PZT stack and flange. With the integrated structure, the effect of reducing the contour dimension of the ultrasonic driving surgical device can be obtained, and the outer diameter is reduced to the range of 8-10 mm as compared with the range of 12-15 mm in the prior art, thereby further meeting the application requirements.

3 Claims, 1 Drawing Sheet

(51) Int. Cl.
*A61B 17/00* (2006.01)
*A61B 17/32* (2006.01)

(58) Field of Classification Search
USPC .................................. 310/323.19, 367, 369
See application file for complete search history.

(56) References Cited

U.S. PATENT DOCUMENTS

| | | | | |
|---|---|---|---|---|
| 5,798,599 A * | 8/1998 | Harwood | ............... | B06B 1/0611 |
| | | | | 310/323.01 |
| 6,286,747 B1 * | 9/2001 | Chan | ..................... | B06B 1/0261 |
| | | | | 156/580.1 |
| 6,491,708 B2 * | 12/2002 | Madan | ........... | A61B 17/320068 |
| | | | | 310/334 |

* cited by examiner

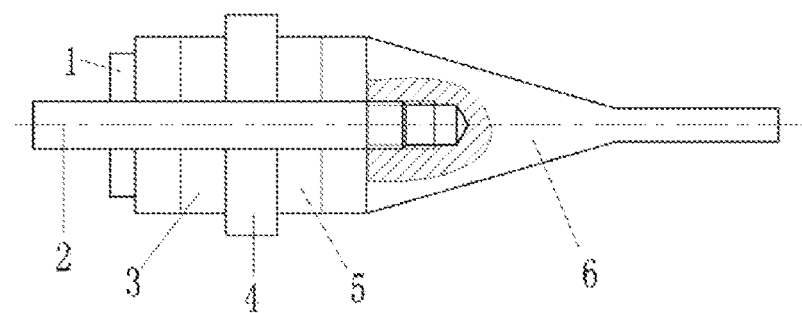
Fig. 1 (Prior Art)
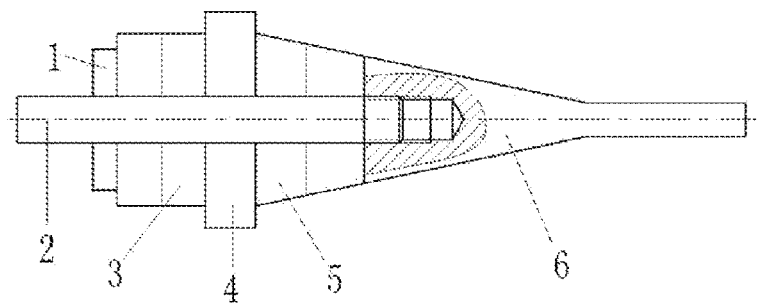
Fig. 2 (Fig. 2 as an illustration in Abstract)
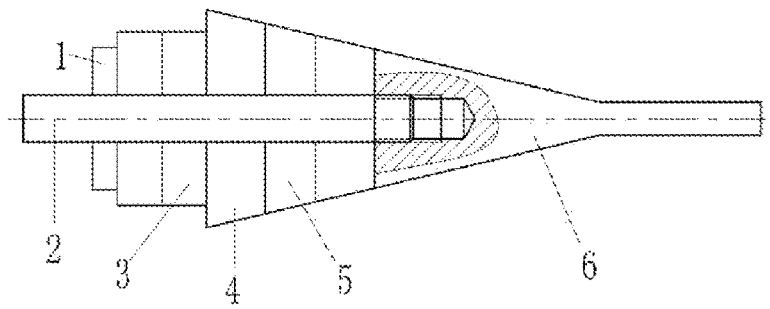
Fig. 3
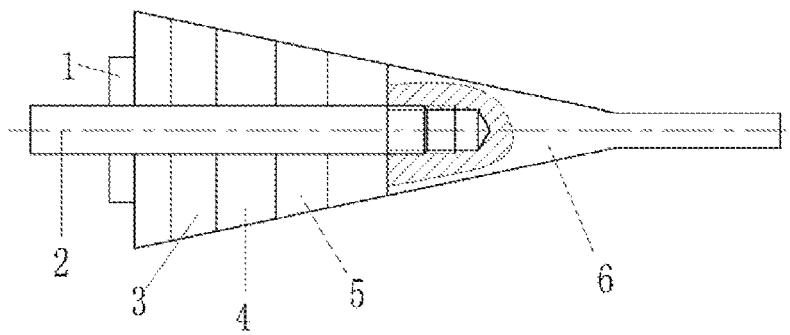
Fig. 4

PZT TRANSDUCER-HORN INTEGRATED ULTRASONIC DRIVING STRUCTURE

TECHNICAL FIELD

The invention belongs to the field of medical ultrasonic driving surgical devices and application thereof, and relates to an ultrasonic vibration device of PZT (piezoelectric ceramic) transducer-horn integrated structure design and assembly.

BACKGROUND ART

Conventionally, a PZT transducer-horn ultrasonic driving structure, as shown in FIG. 1, consists of a nut (1), a bolt (2), a left PZT circular stack (3), a flange (4), a right PZT circular stack (5), and a horn (6). Under the existing PZT material and ultrasonic generation and driving structure conditions, the contour dimension of the driving device is limited within a certain special scale and the outer diameter is relatively large, which can not meet the requirements for minimally-invasive abdominal surgery. For the PZT transducer-horn integrated design and assembly, the dimension of PZT materials on two sides of the flange (4) and the shape of the horn should meet the requirements for ultrasonic vibration node and antinode. The invention changes the design and assembly method in the prior art that the PZT transducer and horn are separated and adopts the PZT transducer-horn integrated structure design and assembly. As shown in FIG. 2, the right PZT stack is designed and assembled to be a part of the horn, so that the dimension of the horn is relatively reduced without changing the overall dimension of PZT, thereby achieving the purpose of reducing the outer diameter of the ultrasonic driving device. It is proven that the outer diameter of the driving device of PZT transducer-horn integrated structure design and assembly method is greatly reduced. FIG. 3 and FIG. 4 represent ultrasonic driving structures of having the design that the flange, left PZT transducer and right transducer and horn are integrated.

SUMMARY OF THE INVENTION

Considering the separated design of PZT transducer and horn of the conventional driving structure, under the existing PZT material and ultrasonic generation and driving structure conditions, the contour dimension of the driving device is limited within a certain special scale, and the outer diameter ranges from 12 mm to 15 mm, resulting in the problem of not meeting the requirements for desired minimally-invasive abdominal surgery. As the dimension of PZT materials on two sides of the flange (4) and the shape of the horn need to meet the requirements for ultrasonic vibration node and antinode, the PZT transducer-horn separated design and structure is changed and replaced by the PZT transducer-horn integrated structure design and assembly.

In the piezoelectric transducer-horn integrated design, the right PZT stack (5) is designed and assembled to be a part of the horn, so that the dimension of the horn is relatively reduced without changing the overall dimension of PZT, thereby achieving the purpose of reducing the outer diameter of the ultrasonic driving device. Specifically, the structure is as follows:

A PZT transducer-horn integrated ultrasonic driving structure, comprises a nut, a bolt, a left PZT circular stack, a flange, a right truncated stack and a horn; and the horn, the right PZT truncated stack, the flange and the left PZT circular stack are arranged in sequence and then connected via the bolt and fastened via the nut, the right PZT truncated stack is a truncated cone-shaped stack formed by PZT circular plates, and the right PZT truncated stack and the horn are integrated to form the ultrasonic driving structure. The design is carried out on the basis that the dimension of PZT materials on two sides of the flange and the shape of the horn meet the requirements for ultrasonic vibration node and antinode, the dimension of round contour of the circular PZT transducer and flange is reduced so that the thickness of the truncated PZT transducer and flange stack is increased.

Further, the PZT transducer-horn integrated ultrasonic driving structure may be that: the flange is truncated cone-shaped and integrated with the right PZT transducer and horn to form the ultrasonic driving structure.

Furthermore, the PZT transducer-horn integrated ultrasonic driving structure may be that: the left PZT transducer is truncated cone-shaped and integrated with the flange, right PZT transducer and horn to form the ultrasonic driving structure.

Advantageously, the PZT transducer-horn integrated structure can provide the effect of reducing the contour dimension of the ultrasonic driving device, reduce the outer diameter to the range of 8-10 mm as compared with the range of 12-15 mm in the prior art, thereby meeting the application requirements.

DESCRIPTION OF DRAWINGS

FIG. 1 is a schematic diagram of the conventional PZT transducer-horn structure.

FIG. 2 is a schematic diagram of a right PZT transducer/horn integrated structure.

FIG. 3 is a schematic diagram of a flange/right PZT transducer/horn integrated structure.

FIG. 4 is a schematic diagram of a left PZT transducer/flange/right PZT transducer/horn integrated structure.

In the FIG. 4, 1: nut, 2: bolt, 3: left PZT circular stack, 4: circular flange, 5: right PZT circular stack, 6: horn

DETAILED DESCRIPTION OF THE PREFERRED EMBODIMENTS

According to the invention, the piezoelectric transducer and the horn in an ultrasonic driving medical device are integrally designed such that without changing the overall dimension of PZT, the flange and PZT stacks are respectively designed and assembled to be a part of the horn, the PZT stacks having both electrical and mechanical conversion function and amplitude amplification function, and the dimension of the horn is relatively reduced, thereby achieving the purpose of reducing the outer diameter of the ultrasonic driving device.

An embodiment is as follows: a PZT transducer-horn integrated ultrasonic vibration structure, consists of a nut (1), a bolt (2), a left PZT circular stack (3), a circular flange (4), a right PZT truncated stack (5) and a horn (6); the horn (6), the right PZT truncated stack (5), the flange (4) and the left PZT circular stack (3) are arranged in sequence and serially connected via the bolt (2) and then fastened via the nut (1). As shown in FIG. 2, the right PZT structure is a truncated cone-shaped stack instead of a right PZT circular stack, and the PZT transducer and the horn are integrally designed and assembled such that the dimension of PZT materials on two sides of the flange (4) and the shape of the horn meet the requirements for ultrasonic vibration node and antinode, with the dimension of circular contour being reduced to increase the thickness of the right PZT truncated stack (5), and the number of the left PZT circular stack is equal to that of the right PZT truncated stack, and the stacks are bonded rigidly enough to ensure high efficiency of electrical-to-mechanical energy conversion of the PZT transducer.

The PZT transducer-horn integrated structure of the invention has three types. The PZT transducer-horn integrated ultrasonic driving structure as set forth may be that: the flange is truncated cone-shaped and integrated with the right PZT transducer and horn to form the ultrasonic driving structure. Further, the two PZT transducer-horn integrated ultrasonic driving structures as set forth may be that: the left PZT transducer is truncated cone-shaped and integrated with the flange, right PZT transducer and horn to form the ultrasonic driving structure.

The PZT transducer-horn integrated structure design and assembly method provides the significant effect of reducing the contour dimension of the ultrasonic driving surgical device, and the outer diameter is reduced to be less than 10 mm as compared with the range of 12-15 mm in the prior art, thereby meeting the application requirements. The PZT transducer-horn integrated ultrasonic driving method of the invention can also be applied to other small-sized ultrasonic driving devices.

We claims:

1. A PZT transducer-horn integrated ultrasonic driving structure, comprising a nut, a bolt, a left PZT circular stack, a flange, a right PZT truncated stack and a horn, characterized in that the horn, the right PZT truncated stack, the flange and the left PZT circular stack are arranged in sequence and connected via the bolt and then fastened via the nut, the right PZT transducer is a truncated cone-shaped stack formed by PZT circular plates, and the right PZT transducer and the horn are integrated to form the ultrasonic driving structure;

wherein the dimension of PZT on two sides of the flange and the horn needs to meet the requirements for ultrasonic vibration node and antinode, according to the requirements, the dimension of round contour of the PZT circular stack is reduced, and the dimension of round contour of the flange is reduced, so that the thickness of the PZT truncated stack is increased and the thickness of the flange stack is increased.

2. The PZT transducer-horn integrated ultrasonic driving structure according to claim 1, wherein the flange is truncated cone-shaped and integrated with the right PZT transducer and the horn to form the ultrasonic driving structure.

3. The PZT transducer-horn integrated ultrasonic driving structure according to claim 1, wherein the left PZT transducer is truncated cone-shaped and integrated with the flange, the right PZT transducer and the horn to form the ultrasonic driving structure.

* * * * *